(12) United States Patent
Byon et al.

(10) Patent No.: US 6,747,015 B2
(45) Date of Patent: Jun. 8, 2004

(54) LOW MOLECULAR WEIGHT POLYMANNURONATE

(75) Inventors: Jae Hyong Byon, Busan (KR); Jin Woo Lee, Busan (KR); Dong Soo Lee, Shiheung-Shi (KR); Taek Jeong Nam, Busan (KR)

(73) Assignee: KBP Co., Ltd., Kyungki-do (KR)

( * ) Notice: Subject to any disclaimer, the term of this patent is extended or adjusted under 35 U.S.C. 154(b) by 0 days.

(21) Appl. No.: 09/970,043

(22) Filed: Oct. 2, 2001

(65) Prior Publication Data

US 2002/0137723 A1 Sep. 26, 2002

Related U.S. Application Data

(63) Continuation-in-part of application No. PCT/KR01/00139, filed on Feb. 1, 2001.

(30) Foreign Application Priority Data

Feb. 3, 2000 (KR) .......................................... 2000-5294
Dec. 28, 2000 (KR) ......................................... 2000-83853

(51) Int. Cl.$^7$ ..................... A01N 43/04; A61K 31/715; C08B 37/04
(52) U.S. Cl. .......................... 514/54; 514/779; 514/866; 514/911; 536/3; 426/575
(58) Field of Search .................. 426/575, 2; 514/54, 514/779, 866, 911; 536/3; 524/28

(56) References Cited

U.S. PATENT DOCUMENTS

| | | | |
|---|---|---|---|
| 3,861,400 A | | 1/1975 | Perkins et al. |
| 3,887,562 A | | 6/1975 | Barrachina |
| 4,689,322 A | | 8/1987 | Kulbe et al. |
| 5,283,076 A | | 2/1994 | Kazuki et al. |
| 5,324,526 A | * | 6/1994 | Iwata et al. |
| 5,639,467 A | * | 6/1997 | Dorian et al. |
| 5,656,468 A | | 8/1997 | Dorian et al. |
| 6,121,441 A | * | 9/2000 | Simensen et al. |
| 6,274,566 B1 | * | 8/2001 | Eliaz et al. |

FOREIGN PATENT DOCUMENTS

| | | |
|---|---|---|
| CN | 1075864 A | 9/1993 |
| CN | 1099235 A | 3/1995 |
| EP | 0136502 A2 | 4/1985 |
| EP | 0 493 265 A | 7/1992 |
| EP | 0 506 326 A | 9/1992 |
| GB | 2 325 233 A | 11/1998 |
| JP | 58021402 | 2/1983 |
| JP | 63239207 | 10/1988 |
| JP | 6007093 A2 | 1/1994 |
| JP | 6172375 | 6/1994 |
| JP | 06172375 | 6/1994 |
| JP | 06217774 | 8/1994 |
| JP | 10316521 | 12/1998 |
| JP | 11080204 | 3/1999 |
| WO | WO 91 11205 A | 8/1991 |
| WO | WO 95 24497 A | 9/1995 |
| WO | WO 98 51710 A | 11/1998 |

OTHER PUBLICATIONS

Lee, et al., Effect of Low–Molecularization on Rheological Properties of Alginate, 1998, 31 (1), 82–89, J. Korean Fish. Soc.

Lee, et al., Uronate Compositions of Alginates from the Edible Brown Algae, 1998. 31 (1), 1–7, J. Korean Fish. Soc.

Lee, et al., Effect of Low–Molecular Alginates on Cholesterol on Cholesterol Levels and Fatty Acid Compositions of Serum and Liver Lipids in Cholesterol–Fed Rats, 1998, 31 (3), 399–408, J. Korean Fish. Soc.

Kimura, Effects of soluble sodium alginate on cholesterol excretion and glucose tolerance in rats, 1996. 47–54, Journal of Ethno–pharmacology.

Choi, et al., 1991, 173–178, Journal of Korea Geriatric Soc.

Simple Melecules in Biology (Altschuler BIOS 300 claa 3), http//www.bios.niu.edu/altschuler//image/b300c3.html.

Haraguchi, et al., Purification and properties of poly(<beta>—D—mannuronate)lyase from *Azotobacter chroococcum*, 1995, Abstract vo. 44, Issue 5, 576–581, Springer—Verlag.

Choi, et al., "Anti–aging effects of Algin", Journal of Korea Geriatric Society (1991) 1(2) pp. 173–178, (abstract).

A Cardiovascular Support System Containing Potent Antioxidants, http://healthy.hypermart.net/heart.html (2002).

Park, et al., "Effect of ph Drug Release from Polysaccharide Stirred Cell", Drug Delivery, (1998)(abstract).

Ochi, et al., "A Simple Method for Preparation Of Poly–Mannuronate Using Poly–Guluronate Lyase", 1995, Biosci. Biotech. Biochem., vol. 59, No. 8, pp. 1560–1561.

Haug, et al., "Studies on the Swquence of Uronic Acid Residues in Alginic Acid", 1967, Acta Chem. Scand., vol. 21, No. 3, pp. 691–704 (XP009006155).

* cited by examiner

*Primary Examiner*—James O. Wilson
*Assistant Examiner*—Traviss C. McIntosh, III
(74) *Attorney, Agent, or Firm*—Knobbe, Martens Olson & Bear LLP

(57) ABSTRACT

Disclosed is a polymannuronate composition including polymannuronate having molecular weight from about 4,000 to about 500,000 in a high purity. The composition can be used in producing nutritional compositions such as functional foods and health aids. Also, the composition can be used in a pharmaceutical composition along with a pharmaceutical carrier. The composition has various effects, including controlling serum lipids, preventing hyperlipidemia, preventing obesity, preventing diabetes, enhancing functions of liver, expelling heavy metals from a body, etc. Further disclosed is a process to producing the polymannuronate composition, in which alginate is hydrolyzed and then the polymannuronate components are isolated. Further disclosed herein is a composition produced by that process. In the hydrolysis, an organic acid is preferably used, and the isolation of the polymannuronate involves adjustment of pH of the resulting mixture of the hydrolysis.

34 Claims, No Drawings

LOW MOLECULAR WEIGHT POLYMANNURONATE

RELATED APPLICATIONS

This application is a continuation-in-part under 35 U.S.C. §356(c) claiming the benefit of the filing date of PCT Application No. PCT/KR01/00139 designating the United States, filed Feb. 1, 2001 and published in English as WO 01/56404 A1 on Aug. 9, 2001, which claims the benefit of the earlier filing dates of Korean Patent Application No. 2000/5294, filed Feb. 3, 2000 and Korean Patent Application No. 2000/83853, filed Dec. 28, 2000. The publication WO 01/56404 is incorporated herein by reference.

BACKGROUND OF THE INVENTION

1. Field of the Invention

The present invention relates to low molecular weight polymannuronate, and more particularly, the present invention relates to an isolated low molecular weight polymannuronate composition, and a process for preparing thereof from high molecular weight alginate. Further, the present invention pertains to a nutritional composition and a pharmaceutical composition comprising the composition, and a method of treatment of certain conditions using thereof.

2. Description of the Related Art

The incidence of many cardiovascular diseases that are hard to treat such as hypertension, arteriosclerosis, angina pectoris, myocardial infarction and cerebral thrombosis, as well as obesity and diabetes, are increasing due to excessively nutritional diet which includes high fat and high protein, and lack of exercise. There are increasing interests in the prevention and treatment of such diseases. It is preferable to prevent and/or treat these diseases or conditions with dietary foods supplemented with extracts from natural sources rather than with artificially synthesized products because such natural products are normally considered safe and more desirable by the consumer.

Reflecting such trends, there have been much research and development focusing on dietary fibers. Certain dietary fibers were known to have favorable effects on the prevention of constipation and obesity as well as the prevention of geriatric diseases such as thrombosis, arteriosclerosis and hyperlipidemia. J. Ame. Clin. Nutr. 48:748–753, 1988; J. Ame. Clin. Nutr. 52:495–499, 1990; J. Ame. Clin. Nutr. 124:78–83, 1994.

Among dietary fibers, high molecular weight alginate, a dietary fiber component constituting 20–30% of the cell-wall polysaccharides in marine algae (e.g. brown seaweed, sea tangle, gulfweed, hiziki), was known as having effects on lowering cholesterol levels in vivo and repressing obesity. J. Jap. Nutr. 26(3):78–83, 1974; J. Jap. Nutr. 33(6):273–281, 1974; Jap. J. Fisheries 59(5):879–884, 1993.

At present, many alginate-containing products are being manufactured and sold. However, the alginates contained in the products are produced by simple extraction and processing from raw seaweed materials, and are of high molecular weight, which is more than about 4 million daltons. High molecular weight alginate is a block polymer of mannuronate (M) and guluronate (G) monomers. The alginate in its high molecular weight form has high viscosity and low solubility in water. With the high viscosity and low water solubility, it is not easy to add the high molecular form of alginate to foods (especially into beverages) in high concentrations.

Japanese Laid-Open Patent Publication Hei 6-7093 discloses a use of low molecularized alginate as supplement to functional drinks. The term "low molecularized alginate" as used herein refers to the state in which polyguluronate and polymannuronate of Mw. 10–900 kDa are mixed. Compared with high molecular weight alginate, low molecularized alginate is known to have lower viscosity and higher solubility, and to have increased beneficial effects on cholesterol levels.

Conventional methods used to prepare low molecularized alginate from high molecular forms include acid-alkali hydrolysis method [Haug, A., Larsen, B. and Smidsrod, O., Acta Chem. Scand., 20(1):183–190, 1966; Hirst, E. and Rees, D. A. J. Chem. Soc., 9:1182–1187, 1965; Hirst, E. L., Percival, E. and Wold, J. K. J. Chem. Soc., 8:1493–1499, 1964], hydrolysis under heat and pressure [Japanese Patent Laid-Open Publication Hei 6-7093, 1994; Kimura, Y., Watanabe, K. and Okuda, H., J. Ethnopharmacology 54:47–54,1996] and hydrolysis by enzymes [Doubet, R. S. and Quatrano, R. S., Appl. Environ. Microbiol. 47(4):699–703, 1984; Dunne, W. M. and Buckmire, F. L. A., Appl. Environ. Microbiol. 50(1):562–567, 1985; Hansen, J. B. and Nakamura, L. K. Appl. Environ. Microbiol. 49(4):1019–1021, 1985; Haug, A. and Larsen, B., Carbohydr. Res. 17:297–308, 1971; Romeo, T. and Preston, J. F., Biochemistry 25(26):8385–8391, 1986; Yonemoto, Y., Murata, K., Kimura, A., Yamaguchi, H. and Okayama, K., J. of Fermen. and Bioengin. 72(3):152–157, 1991].

The acid-alkali hydrolysis method is difficult to adapt to industrial scale due to deterioration of product quality, corrosion of reactors, need for a substantial amount of neutralizing agents and troublesome handling of strong acids. The second method for preparing low molecularized alginate by heating alginate at 100–200° C. under pressure, also has defects, in that the reaction takes a long time and is costly because the process is carried out at high temperatures of more than 100° C. under high pressure. The enzyme-hydrolysis method is not appropriate for industrialization due to long reaction time.

As mentioned above, compared with high molecular weight alginate, low-molecularized alginate has increased effects on decreasing cholesterol levels and has improved physical properties such as solubility. Thus, the low molecularized alginate is expected to be useful for health-aid foods.

The low-molecularized alginate is a mixture including polymannuronate, polyguluronate, and some copolymers of the mannuronate and guluronate. However, polymannuronate in an isolated form is not known. Nor is it known what effects it will have on decreasing cholesterol levels. Polymannuronate is only known in its calcium salt as a material for controlling the levels of toxic elements in patients with chronic uremia (Kulbe et al., U.S. Pat. No. 4,689,322), or as a cell- or tissue-coating material to protect transplanted cells or tissue following transplantation (Dorian et al., U.S. Pat. No. 5,656,468).

SUMMARY OF THE INVENTION

One aspect of the present invention provides a method of preparing a polymannuronate composition. The method comprises: providing alginate; hydrolyzing the alginate to form a mixture comprising polymannuronate and polyguluronate, wherein the polymannuronate has a molecular weight ranged from about 4,000 to about 500,000; and isolating the polymannuronate from the mixture.

In the method, the provision of the alginate comprises extracting the alginate from marine algae. The alginate has a molecular weight from about 2,000,000 to about 4,000,000. The hydrolysis is carried out for about 20 minutes to about 3 hours. Alternatively, the hydrolysis is carried out for about 40 minutes to about 2 hours, or for about 1 hour to about 1.5 hours. The hydrolysis comprises adding one or more acids to the alginate and heating the mixture of the alginate and the acid. A representative group of organic acid is selected from the group consisting of citric acid, malic acid, oxalic acid, lactic acid, succinic acid, tartaric acid and acetic acid. Preferably, the organic acid is acetic acid. The concentration of the organic acid is preferably from about 0.2 M to about 0.6 M. The acids at 0.4 M concentration have pH from about 3.2 to about 4.0, preferably from about 3.4 to about 3.8. Preferably, the acids are organic acids. Following hydrolysis, the isolation of polymannuronate comprises adjusting pH of the mixture to a range from about 2.5 to about 3.5. Preferably, the pH of the mixture is adjusted to a range from about 2.8 to about 3.0. The isolation of polymannuronate further comprises forming a precipitate in the mixture and collecting a supernatant, in which the polymannuronate is dissolved, and further comprises precipitating the polymannuronate from the collected supernatant.

A further aspect of the present invention provides a polymannuronate composition prepared by the method. The polymannuronate prepared by the method has a molecular weight from about 4,000 to about 500,000. Preferably, the molecular weight is from about 10,000 to about 100,000, and more preferably from about 25,000 to about 80,000, furthermore preferably from about 40,000 to about 50,000. The polymannuronate composition has a purity from about 70 wt. % to about 98 wt. %. Preferably, the purity is from about 80 wt. % to about 97 wt. %, more preferably from about 90 wt. % to about 95 wt. %. The viscosity of the 2% (w/v) polymannuronate composition dissolved in water at 25° C. is from about 1.25 to about 15. Preferably, the viscosity ranges from about 2 to about 10, more preferably from about 3 to about 7.

Another aspect of the present invention is to provide a polymannuronate composition. The polymannuronate has a molecular weight from about 4,000 to about 500,000. Preferably, the molecular weight is from about 10,000 to about 100,000, and more preferably from about 25,000 to about 80,000, furthermore preferably from about 40,000 to about 50,000. The polymannuronate composition has a purity from about 70 wt. % to about 98 wt. %. Preferably, the purity is from about 80 wt. % to about 97 wt. %, more preferably from about 90 wt. % to about 95 wt. %. The viscosity of the 2% (w/v) polymannuronate composition dissolved in water at 25° C. is from about 1.25 to about 15. Preferably, the viscosity ranges from about 2 to about 10, more preferably from about 3 to about 7.

Still another aspect of the present invention provides a nutritional composition comprising a foodstuff and polymannuronate having a molecular weight from about 4,000 to about 500,000. In case the nutritional composition comprises polyguluronate, the polyguluronate is in an amount less than about 30 wt. % of the total weight of the polymannuronate and polyguluronate. The polyguluronate amount is preferably less than about 15 wt. %, more preferably less than about 10 wt. % of the total weight of the polymannuronate and polyguluronate. The nutritional composition contains the polymannuronate in an amount from about 0.00001 wt. % to about 50 wt. %, and preferably from about 0.0001 wt. % to about 15 wt. %. The foodstuff is in a liquid or solid form. The polymannuronate has a molecular weight from about 10,000 to about 100,000. Preferably the molecular weight is from about 25,000 to about 80,000, more preferably from about 40,000 to about 50,000.

Still another aspect of the present invention provides a pharmaceutical composition comprising polymannuronate and a pharmaceutical carrier, wherein the polymannuronate has a molecular weight from about 4,000 to about 500,000. In the pharmaceutical composition, in case the pharmaceutical composition comprises polyguluronate, the polyguluronate is in an amount less than about 30 wt. % of the total weight of the polymannuronate and polyguluronate. The polymannuronate has a molecular weight from about 10,000 to about 100,000. Preferably the molecular weight is from about 25,000 to about 80,000, more preferably from about 40,000 to about 50,000.

Still further aspect of the present invention provides a method of treatment selected from the group consisting of controlling a cholesterol level in blood, controlling serum lipids, preventing hyperlipidemia, preventing obesity, preventing diabetes, enhancing functions of liver and expelling heavy metals from a body. The method comprising administering a composition comprising a pharmaceutically effective amount of polymannuronate and a pharmaceutically acceptable carrier, wherein the polymannuronate has a molecular weight from about 4,000 to about 500,000. Again, the polymannuronate has a molecular weight from about 10,000 to about 100,000. Preferably the molecular weight is from about 25,000 to about 80,000, more preferably from about 40,000 to about 50,000. In case the composition further comprises polyguluronate, the polyguluronate is in an amount less than 30 wt. % with reference to a total weight of the polymannuronate and polyguluronate.

DETAILED DESCRIPTION OF THE PREFERRED EMBODIMENT

Polymannuronate, a polymer of mannuronic acid, exists as part of alginate, which is a block copolymer including polymannuronate blocks, polyguluronate blocks and blocks made of mixture of mannuronic and guluronic acids. To date no relatively pure form of polymannuronate exists. In a hydrolyzed form of alginate discussed above in Background of the Invention, polymannuronate exists in an amount from about 40 wt. % to about 60 wt. % in a mixture of polymannuronate, polyguluronate and other polymers from the alginate. The molecular weight of the polymannuronate in the hydrolyzed mixture may significantly vary depending upon the degree of hydrolysis.

In accordance of an aspect of the present invention, alginate having a large molecular weight is hydrolyzed to produce a mixture comprising polymannuronate. This hydrolysis is controlled so as to produce polymannuronate having a molecular weight from about 4,000 to about 500,000 Daltons. The mixture then is treated to isolate a polymannuronate composition having the molecular weight from about 4,000 to about 500,000 Daltons. The molecular weight is advantageously from about 10,000 to about 100,000 Daltons; preferably from about 25,000 to about 80,000 Daltons; more preferably from about 40,000 to about 50,000 Daltons. Advantageously, the isolated polymannuronate composition has a purity from about 70% to about 98% of the total weight of components of alginate. Preferably, the purity is from about 80% to about 97%, and more preferably from about 90% to about 95%.

The isolated polymannuronate composition has good solubility in water or aqueous solution. The solubility in water at 25° C. is from about 90 to about 99, preferably from about 94 to about 98, more preferably from about 95 to about 97. Also, the isolated polymannuronate composition has viscosity, when dissolved in water at a concentration of 2% (w/v), is from about 1.25 to about 15 at 25° C. The viscosity of the composition ranges preferably between about 2 and about 10; more preferably about 3 and about 7.

The isolated polymannuronate composition is also referred to as "low molecular weight polymannuronate" throughout this description. This term "low molecular weight polymannuronate" differs from oligomers of mannuronic acid having the molecular weight from about 500 to about 2000 Daltons and further from the non-isolated mixture including some significant amount of other polymeric materials as well as polymannuronate.

According to the process of preparing the polymannuronate composition of this invention, high molecular weight alginate is partially hydrolyzed with an acid to produce low molecularized alginate, a mixture of polymannuronate, polyguluronate and some other polymeric materials, from which polymannuronate is separated by precipitation dependent on pH.

The high molecular weight alginate to be used as a starting material for the present invention can be obtained from natural brown algae or from a dried-powder sample thereof after a proper preparation method which are well known in the art, i.e., extraction, neutralization, dehydration and drying under reduced pressure. The alginate subjected to the hydrolysis has a molecular weight from about 2 to 4 million Daltons.

The alginate is hydrolyzed preferably with an organic acid although any proper acid can be used instead. The organic acids which can be used for the present invention include, but are not limited to, citric acid, malic acid, lactic acid, oxalic acid, succinic acid, tartaric acid and acetic acid. Any organic acids that can hydrolyze high molecular weight alginate to low molecule weights can be used for the present invention. The degree of hydrolysis may be differentiated dependent on the organic acid chosen, but adjustable by controlling the concentration of the organic acid used and/or the hydrolysis time. As shown in Example 2 below, acetic acid showed the optimum hydrolysis results among various organic acids under the same concentration conditions.

Advantageously concentrations of the organic acid are between 0.2 mole and 2 mole, more preferably between 0.2 mole and 1 mole. The acids at 0.4 M concentration have pH from about 3.2 to about 4.0, preferably from about 3.4 to about 3.8. The hydrolysis of high molecular weight alginate with an organic acid can preferably be performed at a temperature between 80 to 120° C., and more preferably, between 95 to 105° C.

After the hydrolysis, the low-molecular weight polymannuronate composition is isolated. This isolation is performed by adjusting the pH of the mixture resulting from the hydrolysis. The adjustment of the pH is carried out so as to form a precipitate. To adjust the pH, added to the resulting mixture are either acids or bases. Preferably, one or more acids are added to adjust the pH. More preferably, the same acids as used in the hydrolysis are used for the pH adjustment. Most of the polymannuronate remains unprecipitated, and the supernatant is collected and further proceeded to isolate the polymannuronate. Although not limited thereto, the pH of the resulting solution is adjusted preferably to between 2.5 and 3.5, more preferably between 2.8 and 3.0. If the pH is set under 2.5, the purity of the obtained polymannuronate will be high but the yield would be low, and if the pH is over 3.5, the purity of polymannuronate will be lowered. Either the purity or yield may be compromised depending upon the goal. For the purpose of preparing polymannuronate for use in nutritional compositions or pharmaceutical compositions, the above-noted ranges of pH are preferably employed.

The low-molecular weight polymannuronate obtained according to the process of the present invention can be in high purity of over 90 wt. %. However, the purity may occur from about 70 wt. % to about 98 wt. %. Preferably, the purity is from about 80 wt. % to about 97 wt. %, and more preferably from about 90 wt. % to about 95 wt. %. The low-molecular weight polymannuronate has an average molecular weight between 1 and 100 kDa. The low molecular polymannuronate produced according to the present invention is between 25 and 80 kDa, preferably 30 and 50 kDa, more preferably, 35 to 45 kDa.

The present inventors found that the low-molecular weight polymannuronate thus obtained from the method is unexpectedly superior to materials such as high-molecular weight alginate, low-molecular weight alginate or low-molecular weight polyguluronate, in terms of the function to control serum lipid levels. The phrase "to control serum lipid levels" as used herein is intended to include many functions such as lowering the overall cholesterol level, increasing the levels of the advantageous high density lipoprotein (HDL), lowering the levels of low density lipoprotein (LDL) and controlling the levels of triglyceride and phospholipid, both in blood and liver, as well as lowering GOT and GPT values. GOT and GPT values are results of measuring the activities of the enzymes, Glutamic Oxalotransaminase and Glutamic Pyruvictransminase, respectively. As the activities of GOT and GPT are increased in all types of injuries against liver and their increases are very sensitive to all damages, the ability to lower GOT and GPT values means an enhancement of liver function.

In animal experimentation, it was found that the instant low-molecular weight polymannuronate is superior to low-molecular weight alginate and low-molecular weight polyguluronate in terms of the function to control serum lipid levels. Further, it was also found that animal liver is not damaged with continuous and successive administration of low-molecular weight polymannuronate. See Example 3 below. The novel function of low-molecular weight polymannuronate according to the present invention is not only to lower the overall cholesterol level, but also to control advantageously the composition ratio of each type of cholesterol carrier. Further, the low-molecular weight polymannuronate can lower GOT and GPT values, and thus contribute to enhancement of liver function.

In addition, the present inventors found that the low-molecular weight polymannuronate according to the present invention associates with many harmful heavy metals, such as Cd, Pb, Hg, and then eliminates them from the body. The affinity of polymannuronate to harmful heavy metals is much more increased compared with high-molecular weight alginate. In addition, basically, as the binding ability of polymannuronate with water and water-keeping properties are high, polymannuronate is expected to be beneficial for relieving constipation.

Further, the low-molecular weight polymannuronate obtained from the method of the present invention has good water-solubility and viscosity to be used in production of various food products and health aids. Furthermore, it does not retain the peculiar smell and taste of natural brown algae. The low-molecular weight polymannuronate can be used as a functional additive to various foods or the low-polymannuronate powder alone, for the purpose of favorable adjustment of serum lipid levels and prevention and/or treatment of obesity and diabetes. The low molecular polymannuronate prepared according to the present invention may also be used as a material for controlling the levels of toxic elements in patients with chronic uremia, or as a cell- or tissue-coating material to protect the transplanted cell or tissue from immune attack in transplantation.

The low-molecular weight polymannuronate prepared according to the present invention can be used as a main component or an additive or a supplement when various health-aids and/or functional food are produced.

The term "functional food" as used herein, means a functionally-reinforced special food in which the functionality of general food is reinforced with the addition of the low molecular weight polymannuronate of this invention. Functionality of food generally relates to the physical properties and physiological functionality of the additives. The isolated polymannuronate composition according to this invention has an improved viscosity and binding affinity to heavy metals as physical property. Further, the isolated low molecular polymannuronate composition of the present invention has, as a physiological functionality, a function to prevent hyperlipidemia (i.e. resulting from lowering of cholesterol levels), a function to enhance liver function, and so on. Therefore, if the polymannuronate of the present invention is added during preparation of usual foods, the physical and physiological functionality of the usual food will be enhanced. As used herein, the term of "functional food" is defined to include all such functionally-enhanced foods not only in physical properties but also physiological functions. For example, the low-molecular weight polymannuronate of the present invention may be added to the preparation of secondary-processed food, such as ham, in order to increase viscosity of the food and/or to prevent hyperlipidemialobesity. Then, this secondary-processed food added with the present polymannuronate is generally referred to as functional food.

Separate from the definition for functional food, above, the term "health-aids" or "nutritionally special foods" mean health care composition or foods which are made by adding low-molecular weight polymannuronate of this invention to usual foods or by making an ingestable vehicle solely with polymannuronate. The functional foods, health-aids or nutritionally special foods are also referred herein to as a nutritional composition, a medicament or a pharmaceutical composition, depending upon the existence of a pharmaceutical carrier, the amount of the polymannuronate, the purpose of takings, frequency of takings, etc. The health-care foods are generally sought by patients or persons who have high likelihood of disease, to obtain a particular health effect. When treated with the present invention over an extended period of time, health-aid gives particular pharmacological effect just as medicine, but does not provoke a side-effect compared with usual medicine, because it is made of natural food.

For example, by using the function of the present polymannuronate to diet efficiency, the instant nutritional composition can be used to enhance weight loss. In addition, by using the function to enhance liver function, we may produce functionality-reinforced foods or beverage. Also, the polymannuronate according to the invention is applicable for the preparation of a health-aid that can be used as one of diet therapy to lower and/or adjust cholesterol levels in patients of hyperlipidemia or to prevent hyperlipidemia. Examples of other applications include dietary fiber beverage for prevention of constipation, cholesterol-lowering functional bread, flour noodles and margarine. Furthermore, the compositions of this invention can be administered in combination therapies with other agents. When the compositions of this invention are administered in combination therapies with other agents, they may be administered sequentially or concurrently to the patient. Alternatively, pharmaceutical or prophylactic compositions according to this invention may be comprised of a combination of a polymannuronate composition of this invention and another therapeutic or prophylactic agent.

Pharmaceutical compositions of this invention comprise any of the polymannuronate compositions of the present invention, and pharmaceutically acceptable salts thereof, with any pharmaceutically acceptable carrier. Pharmaceutically acceptable carriers include adjuvants and vehicles, such carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions of this invention may be administered orally, parenterally, by inhalation spray, topically, rectally, nasally, buccally, vaginally or via an implanted reservoir. Oral administration is preferred. The pharmaceutical compositions of this invention may contain any conventional non-toxic pharmaceutically-acceptable carriers. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavoring and/or coloring agents may be added.

The pharmaceutical compositions of this invention may also be administered in the form of suppositories for rectal administration. These pharmaceutical compositions can be prepared by mixing the polymannuronate composition of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the polymannuronate compositions of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The low-molecular weight polymannuronate according to the invention is preferably contained in the final nutritional compositions in a proportion between about 0.00001 and about 100% of final products. Preferably, the polymannuronate is included in an amount from about 0.00001 wt. % to about 50 wt. %. More preferably, the amount of the polymannuronate is from about 0.0001 wt. % to about 15 wt. %. A preferred proportion is generally dependent on the group of foods, e.g., more or less of 0.01–5% for drinks, more or less of 10–50% for noodles, more or less of 40–100% for health-aids.

Functional flour-derived foods such as noodles and bread containing low-molecular weight polymannuronate can be prepared by mixing the isolated low molecular weight polymannuronate in powder form and flour, and then subjecting the mixture to normal production of noodles and bread. The term "solid food product" encompasses such functional foods as noodles and bread, but are not limited thereto. Ordinary skilled in the art will be able to easily apply the concept of the given examples to other food substances in view of this disclosure. The compositions including the low-molecular weight polymannuronate according to the invention can be prepared a various forms to be easily administered by using conventional manufacturing method known in the art. Including the above applications, the present low-molecular weight polymannuronate can be used in diverse fields of food industry in its original powder form or a dissolved solution. For example, it can be added in usual beverages to produce functional beverages, can be added in high fat/cholesterol foods, such as ham and sausage, and also can be added in seasonings for meat or a salt.

The present invention will be further described in greater detail by way of the following examples, which are not intended to limit the invention.

EXAMPLE 1

1. Preparation of Low-molecular Weight Polymannuronate from Alginate

About 60 g of alginate (average molecular weight of about 1300 kDa) was mixed with 600 ml of each organic acid solution in each concentration as shown in table 1 to table 6 below. The mixture was stirred and was hydrolyzed at a temperature of about 100° C. for the times indicated in each column of tables (as the concentration of organic acid is inversely proportional to the hydrolysis time, the thicker is the concentration of organic acid, the shorter the hydrolysis time). The resulting low-molecularized alginate solution in the state of a mixture of low-molecular polymannuronate and low-molecular polyguluronate was adjusted to pH 2.8–3.0 with addition of the same organic acid and then centrifuged for separation (the upper liquid section is polymannuronate and the lower precipitation section is polyguluronate). The supernatant was collected, neutralized by addition of sodium carbonate (1 M), added with ethanol up to final concentration of 50% to produce precipitation, and centrifuged to obtain the precipitation.

The obtained precipitation was dissolved in a minimum amount of distilled water (about 200 ml). The resulting solution was adjusted to pH 2.8–3.0 with the same organic acid and centrifuged for separation. The supernatant was neutralized by the addition of sodium carbonate (1M), added with the same volume of ethanol as above to give precipitation, which is separated by centrifugation, to obtain low-molecular polymannuronate.

2. Molecular Weight Measurement of Obtained Polymannuronate

The molecular weight of obtained polymannuronate was measured by using Sepharose CL-4B and Sepharose CL-6B column chromatography ($\phi$ 12 mm×97.6 cm) and Pullulan (Shodex standard P-82) as the standard. The average molecular weight of polymannuronate prepared according to the following procedure was 46.1 kDa.

3. Purity Assay of Obtained Polymannuronate

After dissolving the obtained low-molecular weight polymannuronate in 1% triethylamine solution, the purity and composition of the obtained low-molecular polymannuronate was analyzed by HPLC using a Whatman Partisil 10-SAX anion exchange column (250×4.6 mm i.d.) and using 0.02 mole potassium phosphate buffer (pH 4.6) containing 5% methanol. By standard, chromatogram of guluronate lactone and mannuronate lactone (Sigma Co.) analyzed by the same HPLC as that of the sample analysis was compared with each elution pattern of each sample, to determine purity. The average purity of polymannuronate produced according to the present invention was 91% in 1 hr, 93% in 3 hrs and 96% in 5 hrs depending on hydrolysis time.

EXAMPLE 2

Partial Hydrolysis of High Molecular Weight Alginate with Various Organic Acids

Using diverse kinds of organic acids partial hydrolysis of high-molecular weight alginate was performed for identical hydrolysis time, the result of which is shown in table 1 below. Dependent on the used organic acid, the progress of low-molecularization was differed, obtaining the maximum low-molecularization with the use of acetic acid in the same concentration. Their yields were similar near 80%.

TABLE 1

Relationship between organic acids and molecular weight of polymannuronate

| Organic acid (0.4 M) | Hydrolysis time (hrs.) | Molecular weight (kDa) |
| --- | --- | --- |
| Citric acid | 3 | 24.0 |
| Malic acid | 3 | 53.2 |
| Oxalic acid | 3 | 37.6 |
| Lactic acid | 3 | 33.8 |
| Succinic acid | 3 | 35.4 |
| Tartaric acid | 3 | 33.1 |
| Acetic acid | 3 | 7.5 |

* Reaction was performed under constant temp. of 100° C.

The hydrolysis was performed with diverse concentration of acetic acids (0.2~1.0 M), the results of which is shown in table 2 below. As can be seen from table 2, the degree of hydrolysis of alginate was increased with the increase in the concentration of organic acid. In case of acetic acid, as low as a concentration of 0.2 M is sufficient to produce the low molecular weight polymannuronate of 40 kDa.

TABLE 2

Relationship between acetic acid concentration and produced polymannuronate

| Acetic acid conc.(M) | Hydrolysis time (hrs) | Molecular weight (kDa) |
| --- | --- | --- |
| 0 | 0 | 1,283.0 |
| 0.2 | 3 | 40.0 |
| 0.4 | 3 | 7.5 |
| 0.6 | 3 | 3.8 |
| 0.8 | 3 | 1.9 |
| 1.0 | 3 | 0.6 |

* Reaction was performed under constant temp. of 100° C.

Varying hydrolysis time, the partial hydrolysis of high molecular weight alginate was performed with unvaried concentrations of acetic acid, malic acid, oxalic acid and citric acid, the results of which are shown in Tables 3 to 6, respectively. The degree of low-molecularization increased with extension of reaction time from 10 to 240 minutes. Especially, more rapid hydrolysis (low-molecularization) was achieved at the beginning of reaction (10~60 min).

TABLE 3

Relationship between hydrolysis time and molecular weight of produced polymannuronate (using acetic acid)

| Acetic acid conc.(M) | Hydrolysis time (min) | Molecular Weight (kDa) |
| --- | --- | --- |
| 0.4 | 0 | 1,283.90 |
|  | 10 | 462.1 |
|  | 20 | 185.6 |
|  | 40 | 109.0 |
|  | 55 | 43.2 |
|  | 60 | 32.8 |
|  | 120 | 23.7 |
|  | 180 | 7.5 |
|  | 240 | 4.4 |

* Reaction was performed at constant temp. of 100° C.

TABLE 4

Relationship between hydrolysis time and molecular weight of produced polymannuronate (using malic acid)

| Malic acid conc.(M) | Hydrolysis time (min) | Molecular weight (kDa) |
| --- | --- | --- |
| 0.4 | 0 | 1,283.0 |
|  | 20 | 569.0 |
|  | 40 | 446.1 |
|  | 60 | 234.2 |
|  | 120 | 123.9 |
|  | 180 | 53.2 |
|  | 240 | 24.0 |

* Reaction was performed at constant temp. of 100° C.

TABLE 5

Relationship between hydrolysis time and molecular weight of produced polymannuronate (using oxalic acid)

| Oxalic acid conc.(M) | Hydrolysis time (min) | Molecular weight (kDa) |
| --- | --- | --- |
| 0.4 | 0 | 1,283.0 |
|  | 20 | 465.4 |
|  | 40 | 354.8 |
|  | 60 | 162.8 |
|  | 120 | 82.5 |
|  | 180 | 37.6 |
|  | 240 | 15.4 |

* Reaction was performed at constant temp. of 100° C.

TABLE 6

Relationship between hydrolysis time and molecular weight of produced polymannuronate (using citric acid)

| Citric acid's conc.(M) | Hydrolysis time (min) | Molecular weight (kDa) |
| --- | --- | --- |
| 0.4 | 0 | 1,283.0 |
|  | 20 | 452.4 |
|  | 40 | 332.8 |
|  | 60 | 154.0 |
|  | 120 | 78.5 |
|  | 180 | 24.0 |
|  | 240 | 13.2 |

* Reaction was performed at constant temp. of 100° C.

EXAMPLE 3

The Effect of Low-molecular Polymannuronate (Animal Test)

1. Materials and Methods (1) Composition of Experimental Diet

Compositions and Contents of a basal diet, a cholesterol diet and a experimental diet are shown in table 7 below. The cholesterol diet (control) was prepared by adding 1% cholesterol to basal diet and subtracting the same amount of sucrose from the basal diet. Experimental diet was prepared by adding 1% cholesterol and one selected from a group consisting of 5% low molecular polymannuronate (pM), 5% polyguluronate (pG) and mixture of 2.5% pM and 2.5% pG to basal diet, and by subtracting the corresponding amount of sucrose from basal diet.

TABLE 7

Composition of experimental diet (g/kg)

| Dietary component | basal diet | Control | PM diet | pM + pG diet | PG diet |
|---|---|---|---|---|---|
| Casein | 180 | 180 | 180 | 180 | 280 |
| Rad oil | 80 | 80 | 80 | 80 | 80 |
| Corn oil | 20 | 20 | 20 | 20 | 20 |
| Mineral | 40 | 40 | 40 | 40 | 40 |
| Vitamin | 8.5 | 8.5 | 8.5 | 8.5 | 8.5 |
| Choline chloride | 2 | 2 | 2 | 2 | 2 |
| Cholesterol | 0 | 10 | 10 | 10 | 10 |
| Sodium cholinate | 0 | 2.5 | 2.5 | 2.5 | 2.5 |
| Polymannuronate | 0 | 0 | 50 | 25 | 0 |
| Polyguluronate | 0 | 0 | 0 | 25 | 50 |
| Sugar | 669.5 | 657 | 607 | 607 | 607 |

(2) Experimental Animal

Male Sprague Dawley (SD) rats aged 4 weeks (purchasing from Korean Experimental Animal Institute) were used as test animals in the present experimentation. A total of 50 animals were divided into five groups as indicated in the table 7 above, and each group of animals were fed with the diet for five (5) weeks, the composition of which is shown in the above table 7.

The living condition of test animal was 22±2° C. of room temperature and 65±3% of humidity, which were autoregulated. After five weeks of diet, bloods from test animals were collected, from which serums were separated, and an examination of the levels of cholesterol, of triglyceride, of phospholipid and of low density lipoprotein were performed both in serum and liver sample.

For the test of the levels of cholesterol, of triglyceride, of phospholipid and of low density lipoprotein, kit reagent (produced by Shin-yang Chemical, Inc.) was used, and the food grade diets were used to feed test animals.

(3) Total Cholesterol Level and Free Cholesterol Levels

For examination of total cholesterol and free cholesterol levels in serum and liver extraction sample, 100 μl of serum and liver extraction sample were used for examination by cholesterol CII-test kit and by free cholesterol C-test kit (produced by Shin-yang Chemical, Inc.).

(4) Triglyceride and Phospholipid Levels

For examination of triglyceride and phospholipid levels, 100 μl of serum and liver extraction sample were used for examination by triglyceride G-test kit and by phospholipid C-test kit (produced by Shin-yang Chemical, Inc.).

(5) High-density Lipoprotein and Low-density Lipoprotein Cholesterol Levels

The level of high-density lipoprotein cholesterol was examined by using high-density lipoprotein cholesterol C-test kit (produced by Shin-yang Chemical, Inc., Korea) for 100 μl of serum and liver extraction sample. The level of low-density lipoprotein cholesterol was calculated by subtracting the level of high-density lipoprotein from the level of total cholesterol.

(6) Activities of Glutamic Oxaloacetic Transaminase (GOT) and Glutamic Pyruvic Transaminase (GPT)

The activities were measured by using the GOT and GPT activity test kits for each 100 μl of serum sample taken.

(7) Statistical Evaluation

The data of experiments were statistically processed by calculation of mean and standard deviation for each test group. Statistical significance of each test group was evaluated by Duncan's multiple test (p<0.01).

2. The Obesity-suppressing Effect of Low-molecular Polymannuronate

Weight increases in five test groups of animals were inspected, the results of which is shown in table 8. As can be seen from the table, the test group animals dieted with 5% low-molecular polymannuronate for five weeks resulted in efficient suppression of weight increase, compared with the control group.

TABLE 8

Feed efficiency during the period of 5-weeks of feeding

| Testing group | Body Weight Increase | Feed intake | Feed efficiency |
|---|---|---|---|
| Basal diet | 197.2 | 429.1 | 0.46 |
| Control[1] | 212.6 | 433.8 | 0.49 |
| Polymannuronate[2] | 199.0 | 446.8 | 0.44 |
| Polymannuronate + Polyguluronate[3] | 201.6 | 453.4 | 0.44 |
| Polyguluronate[4] | 200.1 | 442.1 | 0.45 |

[1]Test group dieted with basal diet + Cholesterol 1%.
[2]Test group dieted with basal diet + Cholesterol 1% + Polymannuronate 5%.
[3]Test group dieted with basal diet + Cholesterol 1% + Polymannuronate 2.5% + Polyguluronate 2.5%.
[4]Test group dieted with basal diet + Polyguluronate 5%.

3. Effects on Cholesterol Level

In five test groups of animals were inspected, the results of which is shown in table 9. As can be seen from the table, the test group animals dieted either with 5% low-molecular polymannuronate or with 5% polyguluronate or with both for five weeks resulted in efficient lowering of cholesterol levels compared with the control group. Especially, the degree of lowering cholesterol level was the highest in the group dieted the low-molecular polymannuronate according to the present invention. Also, the lowering effect in the group fed with admixed diet of polymannuronate+ polyguluronate was higher than that in the group fed only with polyguluronate. From these results, it is expected that the essential component in the low molecularized alginate (i.e. admixture of polymannuronate and polyguluronate) that lowers cholesterol levels in the serum and liver is the low-molecular polymannuronate component of the present invention. According to the results of the present test, the diet of low-molecular polymannuronate of the present invention lowered the serum cholesterol level by 46%, and liver cholesterol level by 59% compared with the levels in control group.

TABLE 9

Cholesterol levels in the serum and liver of the rats fed the experimental diet

| Testing group | Serum (mg/dl) | liver (mg/g) |
|---|---|---|
| Basal diet | 35.1 ± 1.3 | 7.4 ± 0.2 |
| Control*1 | 284.2 ± 3.6 | 35.6 ± 0.3 |
| Polymannuronate*2 | 153.3 ± 2.7 | 14.7 ± 0.2 |
| Polymannuronate + polyguluronate*3 | 207.5 ± 3.3 | 19.6 ± 0.2 |
| Polyguluronate*4 | 218.8 ± 3.4 | 22.1 ± 0.3 |

*1, *2, *3 and *4. Refer to the footnote of Table 8

4. Effects on Triglyceride and Phospholipid

The levels of triglyceride and phospholipid in the serum and liver in the five test groups of animals were inspected, the results of which are shown in tables 10 and 11, respectively.

As can be note from table 10, the level of triglyceride in the serum was the highest in cholesterol diet group and the lowest in polymannuronate diet group. The levels of triglyceride in the other two testing feed groups (i.e. admixture feeding and polyG feeding groups) were shown to be similar to that of basal diet group. Similarly, the level in liver extract was the highest in cholesterol diet group and the lowest in polymannuronate diet group.

As can be noted from table 11, the levels of phospholipid in both serum and liver were the highest in cholesterol diet group and the lowest in basal diet group. The levels of phospholipid in all three testing feed groups were lower than that of cholesterol diet group, and particularly, the lowest in polymannuronate diet group.

With the administration of the low-molecular polymannuronate of the present invention, the levels of triglyceride and phospholipid in the serum were decreased by 42% and 48%, respectively, and the levels in liver were decreased by 35% and 40%, respectively, compared with those of control group.

TABLE 10

Triglyceride levels in the serum and liver of rats fed with experimental diet (Means ± S.E.)

| Testing group | serum (mg/dl) | liver (mg/g) |
| --- | --- | --- |
| Basal diet | 62.5 ± 3.4 | 42.3 ± 1.3 |
| Control*1 | 93.3 ± 4.2 | 79.2 ± 2.0 |
| Polymannuronate*2 | 54.3 ± 2.4 | 40.8 ± 1.7 |
| Polymannuronate + polyguluronate*3 | 60.0 ± 2.7 | 49.2 ± 1.9 |
| Polyguluronate*4 | 72.1 ± 2.9 | 51.9 ± 1.9 |

*1, *2, *3 and *4. Refer to the footnote of Table 8

TABLE 11

Phospholipid levels in the serum and liver of rats fed with experimental diet (Means ± S.E.)

| Testing group | serum (mg/dl) | Liver (mg/g) |
| --- | --- | --- |
| Basal diet | 48.9 ± 1.5 | 10.2 ± 0.8 |
| Control*1 | 98.8 ± 3.2 | 24.5 ± 1.5 |
| Polymannuronate*2 | 63.8 ± 2.6 | 14.8 ± 0.9 |
| Polymannuronate + polyguluronate*3 | 68.5 ± 2.9 | 15.7 ± 0.7 |
| Polyguluronate*4 | 68.0 ± 3.0 | 18.6 ± 0.7 |

*1, *2, *3 and *4. Refer to the footnote of Table 8

5. Effects on the Levels of High-density Lipoprotein and Low-density Lipoprotein Cholesterol The levels of high-density and low-density lipoprotein cholesterol both in serum and in liver were investigated in the five groups of animals, the results of which are shown in table 12 and 13.

The level of high-density lipoprotein in serum was the lowest in the cholesterol diet group and the highest in the polymannuronate diet group, whereas the level in liver was the lowest in basal diet group and the highest in the polymannuronate diet group (see table 12).

The levels of low-density lipoprotein both in serum and in liver were the highest in the cholesterol diet group and the lowest in the basal diet group (see table 13). Compared with the cholesterol diet group (control), in the three testing group feeding with polyM and/or polyG diet, the low-density lipoprotein levels were significantly decreased, with the most outstanding decrease in low-molecular polymannuronate diet group.

Compared with the control (cholesterol diet), with the diet of low-molecular polymannuronate according to the invention, the serum levels of high-density lipoprotein cholesterol were increased by 4.5 times and serum levels of low-density lipoprotein cholesterol decreased by 59%. Further, the high-density lipoprotein cholesterol level in liver was increased by 1.2 times, and that of low-density lipoprotein decreased by 47%.

TABLE 12

HDL-cholesterol levels in the serum and liver of rats fed the experimental diet (mean ± S.E.)

| Testing group | HDL cholesterol in serum (mg/dl) | HDL cholesterol in liver (mg/g) |
| --- | --- | --- |
| Basal diet | 27.8 ± 1.1 | 3.3 ± 0.1 |
| Control*1 | 8.6 ± 0.2 | 5.7 ± 0.3 |
| Polymannuronate*2 | 39.4 ± 0.9 | 6.8 ± 0.2 |
| Polymannuronate + polyguluronate*3 | 23.5 ± 0.6 | 5.4 ± 0.4 |
| Polyguluronate*4 | 15.2 ± 0.7 | 4.9 ± 0.3 |

*1, *2, *3 and *4. Refer to the footnote of Table 8

TABLE 13

LDL-cholesterol levels in the serum and liver of rats fed the experimental diet (mean ± S.E.)

| Testing group | LDL cholesterol in serum (mg/dl) | LDL cholesterol in liver (mg/g) |
| --- | --- | --- |
| Basal diet | 7.3 ± 0.3 | 4.1 ± 0.3 |
| Control*1 | 275.6 ± 3.4 | 29.9 ± 0.5 |
| Polymannuronate*2 | 113.9 ± 1.4 | 7.9 ± 0.2 |
| Polymannuronate + polyguluronate*3 | 184.0 ± 2.4 | 14.2 ± 0.3 |
| Polyguluronate*4 | 203.6 ± 2.9 | 17.2 ± 0.3 |

*1, *2, *3 and *4. Refer to the footnote of Table 8

6. Effects of Low-molecular Polymannuronate on Serum GOT and GPT Values

The activities of GOT and GPT in the serum of five testing groups were investigated, the results of which are shown in table 14. As shown in table 14, the effect on lowering GOT and GPT activities is the highest in the low-molecular polymannuronate diet group, i.e. 38% decrease in GOT and 30% decrease in GPT compared with control.

TABLE 14

Activities of GOT and GPT in the serum of the rats fed with the experimental diet (Mean ± S.E.)

| Testing group | GOT (Karmen) | GPT (Karmen) |
| --- | --- | --- |
| Basal diet | 23.6 ± 1.7 | 18.5 ± 1.4 |
| Control*1 | 45.2 ± 2.3 | 23.4 ± 2.5 |
| Polymannuronate*2 | 27.8 ± 2.1 | 16.3 ± 1.5 |
| Polymannuronate + polyguluronate*3 | 31.9 ± 1.8 | 18.5 ± 1.8 |
| Polyguluronate*4 | 33.4 ± 2.0 | 18.8 ± 1.9 |

*1, *2, *3 and *4. Refer to the footnote of Table 8

7. Acute Toxicity Test

To each of 4-week old ICR mouse (80 males), a single dose of 2 g/kg of low-molecular polymannuronate of the present invention was orally administered. After administration, each mouse was carefully observed at each hour during first 6 hours and for 2 weeks, with respect to its general condition, motility, body weight, appearance and symptoms in auto nervous systems. From daily observation for 2 weeks after oral administration, no abnormalities in motility, body weight, tremor and reflex reaction were observed. As a result, LD50 was more than 2000 mg/kg from this acute toxicity test.

EXAMPLE 4

Test on the Heavy Metal Affinity of Polymannuronate

The purified seaweed alginate, polymannuronate and polyguluronate were dissolved in distilled water and their concentration were adjusted to 400 µg/ml. Metal salts were dissolved in distilled water to prepare for the solutions with concentrations of 0 to 50 or 100 mM. Cations used in this study were $Ca^{2+}$, $Cd^{2+}$, $Co^{2+}$, $Cu^{2+}$, $Fe^{3+}$, $Hg^{2+}$, $Mg^{2+}$, $Mn^{2+}$, $Pb^{2+}$, $Rb^{1+}$, $Sr^{2+}$ and $Zn^{2+}$. Four volumes of seaweed alginate, polymannuronate and polyguluronate solution were mixed with one volume of each cation solution, respectively. The mixture was incubated 2 hr at room temperature and centrifuged (1,800×g for 20 min). The concentration of polymer in each supernatant was measured by phenol-sulfuric acid method [Dubois et al., *Anal. Chem.*, 28, 350–356, 1956]. The concentration of precipitated polymer was calculated and its value was used for determination of relative affinity of polymers for cations. Table 15 shows the result.

TABLE 15

The precipitation of polymer by heavy metal ion

| Heavy metal ion | Concentration (nM)* | | |
|---|---|---|---|
| | Polymannuronate | Polyguluronate | Alginate |
| Ca | 8.0 | 8.5 | 17.6 |
| Cd | 3.5 | 3.6 | 3.6 |
| Co | 20.2 | 9.9 | 11.5 |
| Cu | 3.5 | 4.6 | 3.2 |
| Fe | 2.7 | 3.4 | 2.7 |
| Hg | 18.0 | 77.7 | 100< |
| Mg | 100< | 100< | 100< |
| Mn | 37.2 | 90.2 | 63.5 |
| Ru | 15.5 | 16.9 | 24.1 |
| St | 15.6 | 16.6 | 23.1 |
| Zn | 15.2 | 18.3 | 14.5 |
| Pb | 5.2 | 5.5 | 5.3 |

*the concentration of metal ion required to precipitate 50% of polymer from each 400 µg/ml solution of polymer (polymannuronate, polyguluronate and alginic acid)

With reference to the above table 15, the affinities of polymannuronate to Fe, Cu, Cd, Pb and Ca are outstanding, and its affinities to Zn, St [strontium, Sr?], Ru, Hg, and Co are relatively good, while affinity to Mg is weak. Polyguluronate showed similar tendency to polymannuronate except its lower affinity for Mn and Hg. The affinity of alginic acid to heavy metal ions was much lower than that of polymannuronate and polyguluronate.

As discussed, the various aspects of the present invention have many advantages. The process for preparing low-molecular weight polymannuronate according to the invention has advantages over the prior methods using inorganic acid such as HCl or sulfonic acid, in that problems such as corrosion of machinery including reactor due to strong inorganic acids and post-process treatment for neutralization are expelled. The present process is also advantageous over the prior methods using enzyme or high pressure/temperature in terms of hydrolysis time and cost. According to the present process, a highly pure (90% or more) polymannuronate composition can be prepared.

The low-molecular weight polymannuronate according to the present invention has high solubility; has functional effects such as an effect on lowering cholesterol, as an effective ingredient of natural alginate; and does not retain peculiar flavor and taste of natural alginate. Thus, when it is used as additives for the preparation of functional foods and health-aids, the functionality of foods can be controlled more accurately and desired functional effect could be obtained with a use of less amount. Accordingly, it would be one of the best choices for the preparation of functional foods and health-aids.

The present invention has been described with reference to various specific examples. However, it should be understood that numerous variations and modifications are possible to those skilled in the art without departing from the spirit of the present invention, and all such variations and modifications are intended to be within the scope of the claims which follow.

What is claimed is:

1. A method of preparing a polymannuronate composition, comprising:
   providing alginate;
   hydrolyzing the alginate to form a mixture comprising polymannuronate and polyguluronate, wherein the polymannuronate has a molecular weight ranged from about 4,000 Dalton (Da) to about 500,000 Da, wherein the hydrolysis comprises adding one or more organic acids to the alginate and heating the mixture of the alginate and the organic acid, and wherein the organic acid is selected from the group consisting of citric acid, malic acid, oxalic acid, lactic acid, succinic acid, tartaric acid and acetic acid, wherein the hydrolysis is carried out for about 20 minutes to about 3 hours; and
   isolating the polymannuronate from the mixture.

2. The method of claim 1, wherein the alginate is extracted from marine algae.

3. The method of claim 1, wherein the alginate has a molecular weight from about 2,000,000 Da to about 4,000,000 Da.

4. The method of claim 1, wherein the hydrolysis is carried out for about 40 minutes to about 2 hours.

5. The method of claim 1, wherein the hydrolysis is carried out for about 1 hour to about 1.5 hours.

6. The method of claim 1, wherein the polymannuronate has a molecular weight from about 10,000 Da to about 100,000 Da.

7. The method of claim 1, wherein the polymannuronate has a molecular weight from about 25,000 Da to about 80,000 Da.

8. The method of claim 1, wherein the polymannuronate has a molecular weight from about 40,000 Da to about 50,000 Da.

9. The method of claim 1, wherein the organic acid is acetic acid.

10. The method of claim 1, wherein the concentration of the organic acid is from about 0.2 M to about 0.6 M.

11. The method of claim 1, wherein the isolation of polymannuronate comprises adjusting pH of the mixture.

12. The method of claim 11, wherein the pH of the mixture is adjusted to a range from about 2.5 to about 3.5.

13. The method of claim 11, wherein the pH of the mixture is adjusted to a range from about 2.8 to about 3.0.

14. The method of claim 11, wherein the pH adjustment is carried out by adding one or more acids.

15. The method of claim 1, wherein the isolation of polymannuronate comprises forming a precipitate in the mixture and collecting a supernatant, in which the polymannuronate is dissolved.

16. The method of claim 15, wherein the isolation further comprises precipitating the polymannuronate from the collected supernatant.

17. The method of claim 1, wherein the isolation of polymannuronate isolates the polymannuronate with a purity from about 70 wt. % to about 98 wt. %.

18. The method of claim 1, wherein the isolation of polymannuronate isolates the polymannuronate with a purity from about 80 wt. % to about 97 wt. %.

19. The method of claim 1, wherein the isolation of polymannuronate isolates the polymannuronate with a purity from about 90 wt. % to about 95 wt. %.

20. A nutritional composition comprising a foodstuff and polymannuronate having a molecular weight from about 40,000 Da to about 80,000 Da.

21. The nutritional composition of claim 20, wherein the polyguluronate is in an amount less than about 15 wt. % of the total weight of the polymannuronate and polyguluronate.

22. The nutritional composition of claim 20, wherein the polyguluronate is in an amount less than about 10 wt. % of the total weight of the polymannuronate and polyguluronate.

23. The nutritional composition of claim 20, wherein the polymannuronate is in an amount from about 0.00001 wt. % to about 50 wt. %.

24. The nutritional composition of claim 20, wherein the polymannuronate is in an amount from about 0.0001 wt. % to about 15 wt. %.

25. The nutritional composition of claim 20, wherein the foodstuff is in a liquid or solid form.

26. The nutritional composition of claim 20, wherein the foodstuff is selected from the group consisting of beverages, margarine, hams and noodles.

27. The nutritional composition of claim 20, wherein in the event that the nutritional composition additionally comprises polyguluronate, the polyguluronate is in an amount less than about 30 wt. % of the total weight of the polymannuronate and polyguluronate.

28. The nutritional composition of claim 20, wherein the polymannuronate has a molecular weight from about 40,000 Da to about 50,000 Da.

29. A pharmaceutical composition comprising polymannuronate and a pharmaceutical carrier, wherein the polymannuronate has a molecular weight from about 40,000 Da to about 80,000 Da.

30. The pharmaceutical composition of claim 29, wherein in the event that the pharmaceutical composition additionally comprises polyguluronate, the polyguluronate is in an amount less than about 30 wt. % of the total weight of the polymannuronate and polyguluronate.

31. The pharmaceutical composition of claim 29, wherein the polymannuronate has a molecular weight ranged from about 40,000 Da to about 50,000 Da.

32. A method of treatment selected from the group consisting of controlling cholesterol level in blood, controlling serum lipids, hyperlipidemia, obesity, diabetes, and enhancing functions of liver, the method comprising administering a composition comprising a pharmaceutically acceptable carrier and polymannuronate having a molecular weight from about 40,000 Da to about 80,000 Da to a patient in need of such treatment.

33. The method of claim 32, wherein the polymannuronate has a molecular weight from about 40,000 Da to about 50,000 Da.

34. The method of claim 32, wherein in the event that the composition additionally comprises polyguluronate, the polyguluronate is in an amount less than 30 wt. % of the weight of the polymannuronate and polyguluronate.

* * * * *